United States Patent [19]
Mogendovich

[11] Patent Number: 5,139,516
[45] Date of Patent: Aug. 18, 1992

[54] ARTIFICIAL HEART AND METHOD OF OPERATING THE SAME

[76] Inventor: Eugene Mogendovich, 41 Bunker, E. Hannover, N.J. 07936

[21] Appl. No.: 719,918

[22] Filed: Jun. 24, 1991

Related U.S. Application Data

[63] Continuation-in-part of Ser. No. 345,485, May 2, 1989, abandoned, which is a continuation-in-part of Ser. No. 139,203, Dec. 29, 1987, abandoned.

[51] Int. Cl.⁵ .............................................. A61M 1/10
[52] U.S. Cl. ...................................................... 623/3
[58] Field of Search ............................................ 623/3

[56] References Cited

U.S. PATENT DOCUMENTS

| | | | |
|---|---|---|---|
| 3,733,616 | 5/1973 | Willis, Jr. | 623/3 |
| 3,874,002 | 4/1975 | Kurpanek | 623/3 |
| 4,152,785 | 5/1979 | Shumakov et al. | 623/3 |
| 4,222,127 | 9/1980 | Donachy et al. | 623/3 |
| 4,599,083 | 7/1986 | Perlov et al. | 623/3 |
| 4,650,485 | 3/1987 | Della Sala | 623/3 |
| 4,869,656 | 9/1989 | Della Sala | 623/3 |

*Primary Examiner*—Randy C. Shay

[57] ABSTRACT

An artificial heart has two auricle and two ventricle chambers, and actuating diaphragms with an electromagnetic field forming element, so that they expand and contract under the action of electric current applied to the element, or expand and contract under the action of a fluid supplied into a passage between the diaphragms in emergency situations. The above diaphragms passage can be connected through the air-water connector with a source of water, a source of pressure air, and a respiratory system of a person in emergency situations.

10 Claims, 13 Drawing Sheets

ARTIFICIAL HEART AND METHOD OF OPERATING THE SAME

CROSS REFERENCE TO A RELATED APPLICATION

This application is a continuation in part of application Ser. No. 345,485 filed on May 2, 1989, now abandoned, which is continuation-in-part of application Ser. No. 139,203, filed on Dec. 29, 1987, now abandoned.

BACKGROUND OF THE INVENTION

The present invention relates to an artificial heart. Artificial hearts are known in the art.

One of the artificial hearts was developed by R. Jarvik and disclosed in several U.S. Patents. It is known to provide an artificial heart with an expanding and contracting diaphragm which is actuated by a supply of electric current and displaces blood through the heart. This artificial heart possesses the disadvantage in that a patient is always connected with an electric or compressed air source whose size and weight do not allow free movement of the patient. A patient cannot go far away for a long time from the sources of electropneumatic energy, since he or she could need an exchange of the batteries. Furthermore, the known diaphragm produces the blood displacement with such pressure pulse that after a certain time a patient can suffer a stroke or damage to peripheral vessels can occur. An artificial heart must satisfy several requirements. The dynamic requirement is that it must imitate the shape of blood pulse of a natural heart as close as possible, especially its steep front or the speed of pressure increase. The artificial heart shall be reliable in an emergency situation so that when an electric current of the network is shut off or the battery died, it shall be actuated by available sources in the vicinity of a patient. The sources of energy shall be portable and compact so that the sources and the heart actuator can be placed within or on the human body. The artificial heart shall perform its physiological function, be safe and non-damaging to any organs, be durable and reliable, be efficient, and cosmetically and psychologically acceptable. The existing artificial hearts do not satisfy all requirements listed hereinabove, and they can be further improved. It has been also recognized that in the known artificial heart, the patients may suffer from strokes or damages to the peripheral vessels after a certain time. This undesirable effect shall be eliminated as well. One of the main reasons for damages to peripheral vessels is a significant difference between an artificial and natural shapes of a blood pulse.

SUMMARY OF THE INVENTION

Accordingly, it is an object of the present invention to provide an artificial heart which avoids the disadvantages of the prior art.

More particularly, it is an object of the present invention to provide an artificial heart which can be actuated not only by an electric source, but also from other emergency sources which are readily available, so as to make a patient less dependent from just only one power source.

It is also an object of the present invention to provide such an artificial heart which operates in a manner that is very close to the operation of a natural heart.

In keeping with these objects and with others which will become apparent hereinafter, one feature of the present invention resides, briefly stated, in an artificial heart that has two auricle chambers communicating with two ventricle chambers, two diaphragms actuatable by an electric current, and wherein a fluid from a hydraulic or pneumatic source can also be admitted into a passage between the diaphragms, for example alternatingly to the electric source.

When the artificial heart is designed in accordance with the present invention, it can additionally operate from several emergency sources, in the event of failure of the electric source. For example it can operate from a water line in a household, a hospital, an enterprise, from a compressed air line of a compressor, air line of a gas station, air line of an enterprise, or even from a respiratory system of a person who just blows air by his mouth into the diaphragm.

Another feature of the present invention is that the electric source as a permanent source of energy can be formed so that the blood pressure of the blood displaced (circulated) by the inventive artificial heart has a pulse shape which is very close to the pulse shape in a natural heart. In this case the artificial heart of the invention operates similarly to the natural heart and eliminates the danger of strokes or vessel damages almost completely.

The novel features of the present invention are set forth particularly in the appended claims. The invention itself, however, both as to its construction and manner of operation, will be best understood from the following description of preferred embodiments, which is accompanied by the following drawings.

DESCRIPTION OF PREFERRED EMBODIMENTS

Figure 1A:
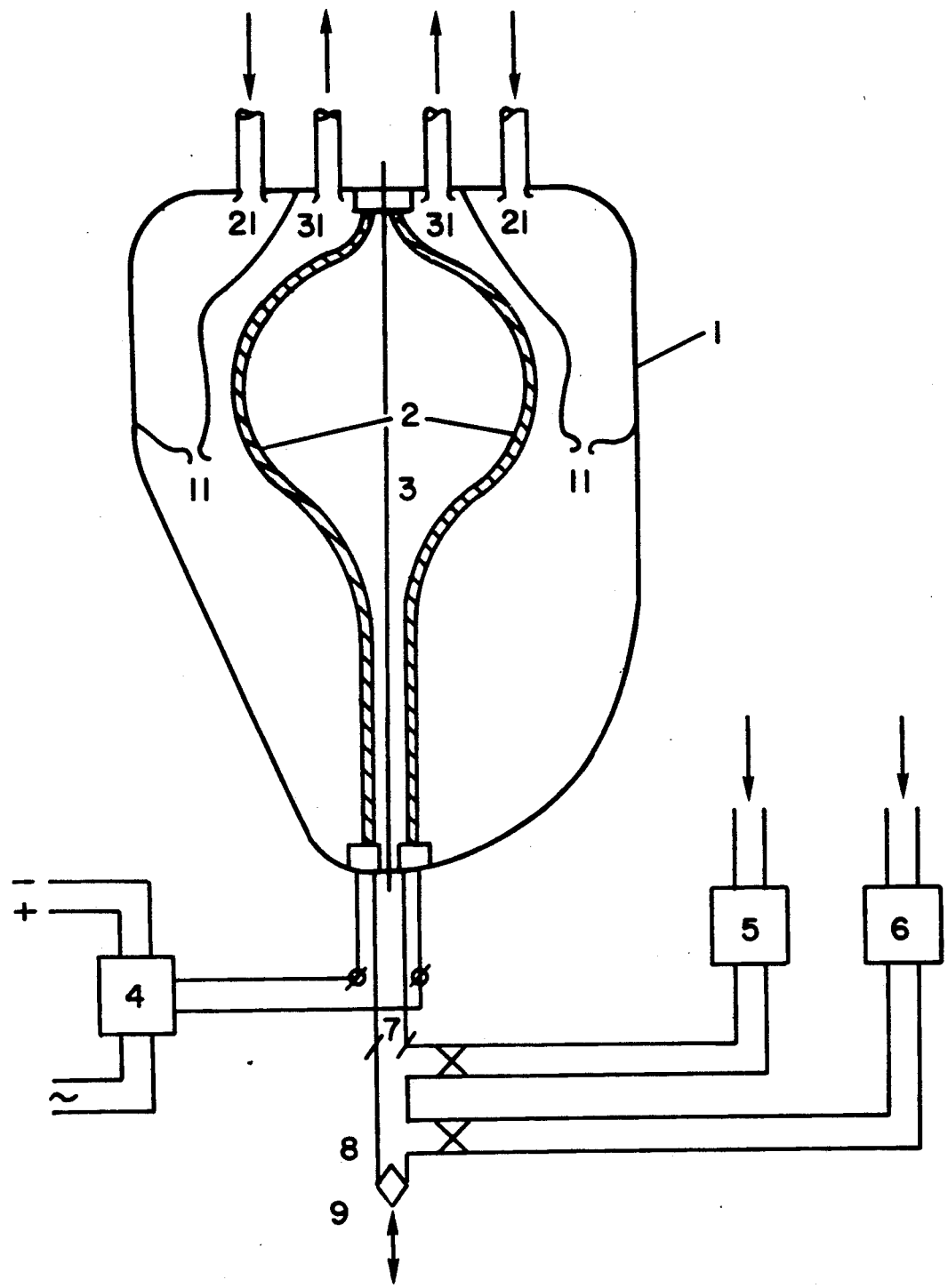
FIGS. 1a, 1b, 1c are schematic views showing an artificial heart in accordance with the present invention in different phases of its operation.

An artificial heart in accordance with the present invention has a rigid housing 1 whose dimensions and shape are close to those of the natural heart. An actuator is located inside the housing 1 and formed as a flexible diaphragms with two walls identified by reference numeral 2 and a passage 3 therebetween. The diaphragms 2 extend through the entire width of the housing 1 normal to the plane of the drawing in FIG. 1a so as to divide the interior of the housing into left and right heart halves. Each heart half is divided by a flexible partition into an auricle chamber and ventricle chamber.

Figure 2:
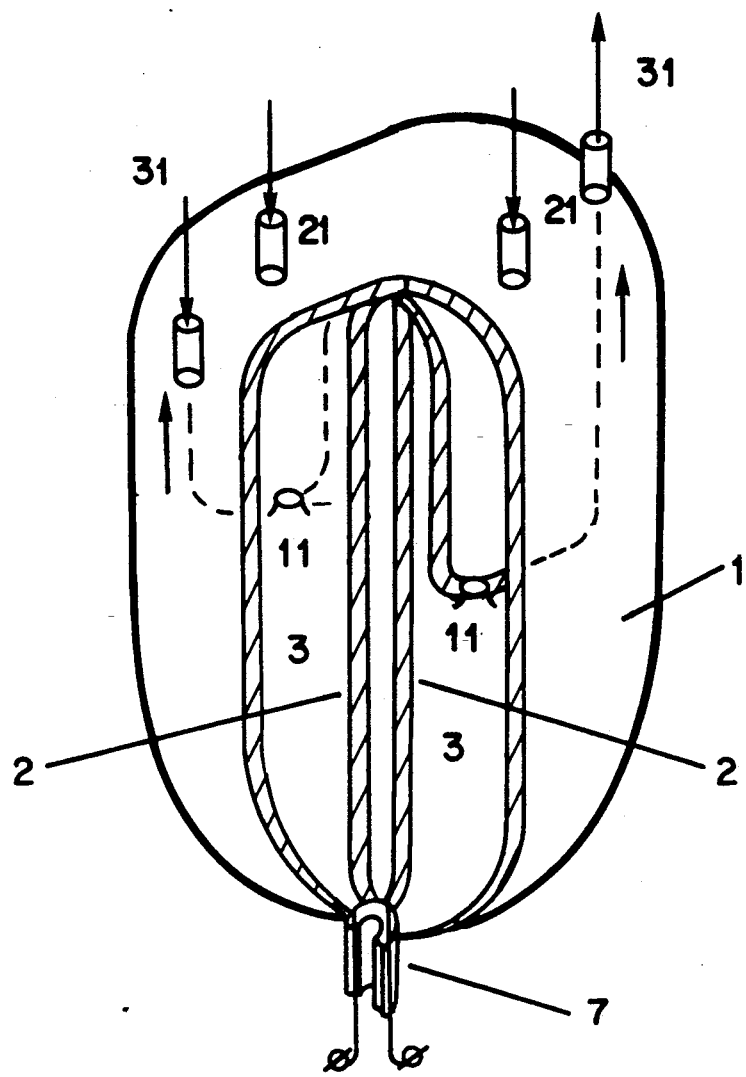
FIG. 2 is a perspective view of the inventive artificial heart.

Check valves 11 are provided in the above rigid partitions to communicate each auricle chamber with the respective ventricle chamber and allow transfer of blood from the former to the latter. Each auricle chamber is provided with a blood inlet 21, and each ventricle chamber is provided with a blood outlet 31. As shown in the three dimensional FIG. 2, the outlet 31 and the valves leading from the auricles are located at the ends of the rigid body of the heart. At the location where the moveability of the diaphragm is the lowest (where they are attached to the body of the heart) and between the body and the auricles, a sufficient passage remains for flowing out of the blood. Check valves can also be arranged in the inlets and outlets of the respective chambers. Such an artificial heart is disclosed for example in U.S. Pat. No. 4,152,785.

Figure 3A:
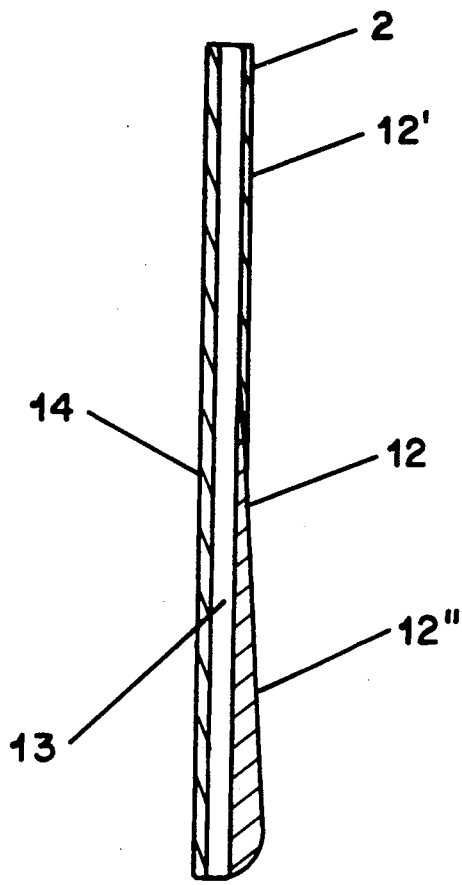
FIGS. 3a, 3b, 3c, 3d show modifications of diaphragms which form an actuating element of the inventive artificial heart.

Each wall 2 of the flexible diaphragm shown in FIG. 3a has a flexible body 12, a coating 13' which can be composed of a ferromagnetic material or other material which can produce an electric field or a magnetic field, and an insolating coating 14. The flexible body 12 has a variable thickness. More particularly, its upper portion 12' is thinner and its lower portion 12" is thicker to impart to the diaphragm a variable flexibility. The upper end of the diaphragm is blind, while the lower end is open and can be provided with a nipple 7.

Figure 3B:
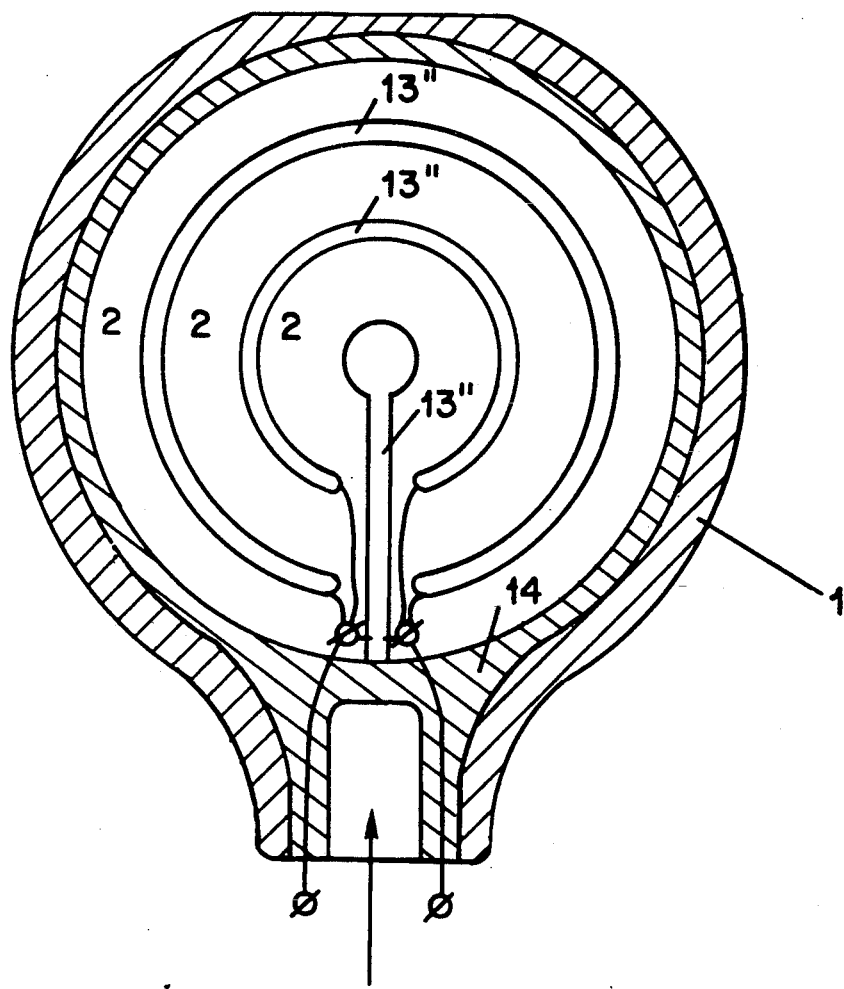
Figure 3C:
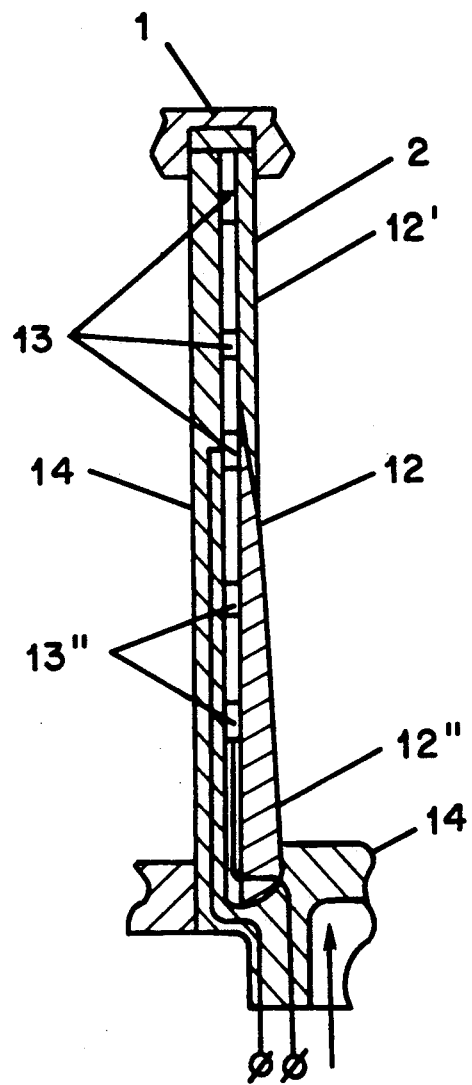

As can be seen from FIG. 3b and FIG. 3c, the flexible diaphragm can be made somewhat differently. While in the embodiment of FIG. 3a the ferromagnetic coating 13' is formed as an uninterrupted layer of a ferromagnetic material, a ferromagnetic coating 13" of the flexible diaphragm of FIGS. 3b and 3c is interrupted. More particularly the ferromagnetic coating 13 is formed by a plurality of coils which are formed by a single spiral shaped ferromagnetic element.

Figure 3D:
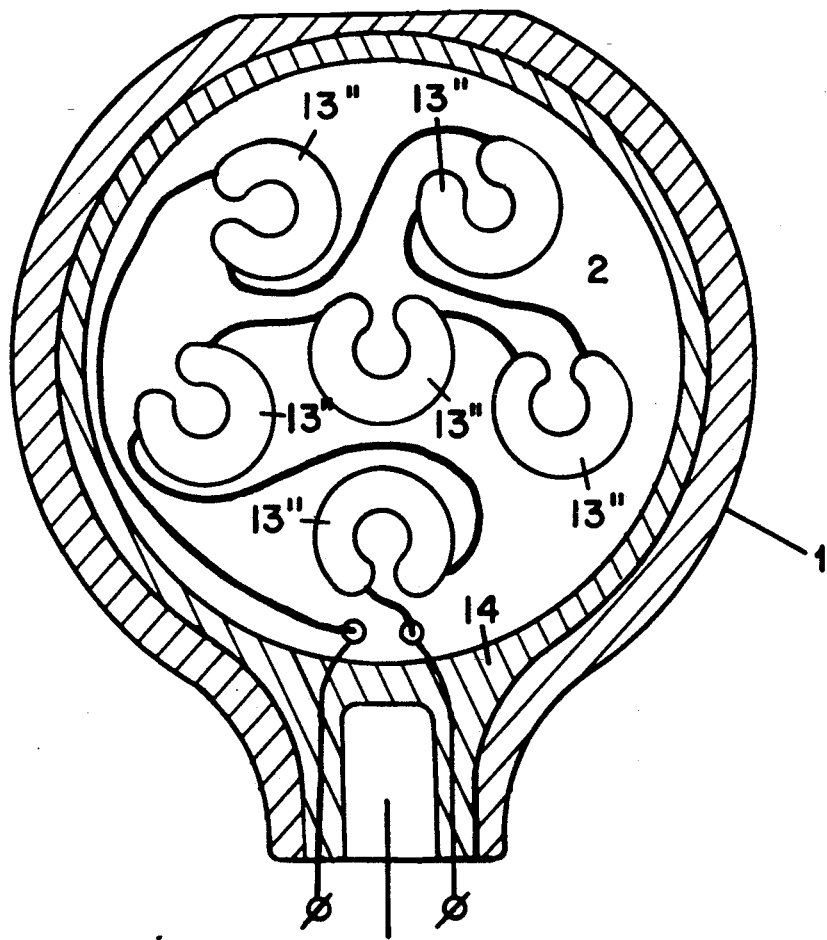

FIG. 3d shows a flexible diaphragm in accordance with a further embodiment of the present invention. Here the ferromagnetic coating is also interrupted as in the embodiment of FIGS. 3b and 3c, but in contrast to FIG. 3b includes a plurality of individual coils which are connected in series. It is to be understood that the diaphragms of this embodiment also has a variable thickness.

The diaphragm and more particularly its coating (uninterrupted or interrupted) are connected with an electro-magnetic converter 4 which, in turn, is connectable with an electric battery or another DC source. The passage 3 of the diaphragm is connected with a pipe with a hydraulic convertor which converts a constant hydraulic pressure into "a"; variable or impulse hydraulic pressure. The passage 3 of the diaphragm is also connected with a pneumatic convertor which converts a constant pneumatic pressure into the variable or impulse pneumatic pressure. Finally, a pipe 9 is also connected with the described above passage 3 and can lead from a respiratory system of any available person. The above mentioned hydraulic convertor and the pneumatic converter are standard devices which are well known in modern technology and can be used in the artificial heart in accordance with the present invention. The hydraulic converter 5 is connectable with a water supply line. The pneumatic, converter 6 is connectable with an air supply, for example an air compressor. On-off valves 8 are provided between the inner passage 3 and the elements 5,6,9. The nipple 7 can serve for screw connection of the respective pipes leading from the elements 5,6,9, so that the latter are easily connectable with the passage 3 and disconnectable from the same. In normal conditions the artificial heart is actuated by electric power via the electromagnetic transformer 4, and the elements 5,6,9 can be either removed from the nipple 7 or disconnected from the passage 3 by the valves 8. In this mode of operation, DC is supplied from an electric source and converted by the convertor 4 into AC which is then supplied to the coating of the walls 2. In the absence of current the walls 2 extend substantially parallel to one another. However, when the above current is applied to the walls, a longitudinal electric current flows in the coatings 13 and forms a transverse magnetic field. When the coatings 13 have identical charges, the walls spread apart from one another and the diaphragm bulges laterally.

The upper thinner portions of the walls are located in the region of the auricle chambers, while the lower thicker walls are located in the region of the ventricle chambers. First the upper portions of the walls stretch and form a steep front of the pulse. Blood is supplied through the valves from the auricle chambers into the ventricle chambers. Then the lower portion of the walls starts to stretch under the action of the pressure of fluid or electromagnetic forces, and blood is expelled from the ventricle chambers into aortas through the valves 31. The auricle chambers are active. During movement of the upper thinner portion of the diaphragm, the auricles are compressed and the blood under pressure is supplied into the ventricles with a high blood velocity and steep pulse front, similarly to the operation of the natural heart.

As for the function of the auricles, they build an initial increased pressure in the ventricles, similarly to the natural heart. This increased pressure in the ventricle makes possible a faster pressing out of blood into aorta, forming a steeper front of the blood pressure wave, and more accurate imitation of the shape of the natural pulse. This is an important feature of the present invention. The thinner portion of the diaphragm has not less than ⅓ of the total area of the diaphragm. The above diaphragm and its operation are described for example in the U.S. Pat. No. 4,222,127, and therefore no further details are believed to be needed for understanding the same.

Figure 4A:
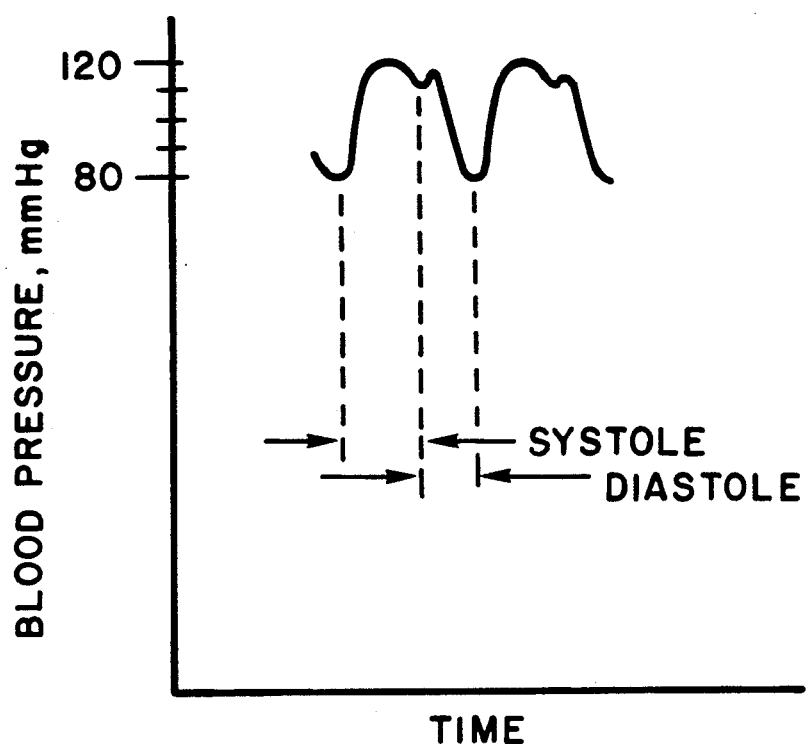
FIG. 4 schematically shows electro pulse and pressure wave formation for the inventive artificial heart.

As mentioned, the important feature of the present invention is that the electromagnetic convertor 4 forms such an electric signal supplied to the coatings of the walls 2, that the shape of the impulse of a blood pressure of the blood which is displaced by the diaphragm is close to the shape of the impulse of a natural blood pressure as shown in FIG. 4. Simultaneously with the elastic movement of the diaphragm which influences the shape of the impulse, also a current which forms the magnetic field between the walls can change. This variable magnetic field can form the impulse with a steep forward front.

In all cases, flowing out of a working fluid from the artificial heart during the interval between the pulses (systole) takes place under the action of two forces, namely a difference between the pressure of blood in the heart during systole and an atmospheric pressure in the drainage line of the control valves, and elastic forces of the diaphragm 2.

During spreading and retracting of the walls the passage 3, either by removal of the elements 5,6,9 or by the opening of the valve 8 in the pipe is relieved. Therefore no vacuum or no excess pressure are formed in the passage during movement of the walls.

In accordance with a further feature of the present invention, the elements 5,6,9 can be connected with the passage 3 of the diaphragms. The diaphragms stretch under the action of impulses of pressure of water from the element 5, or air from the element 6, or air from a respiratory system of a person who breathes into the pipe 9. The impulses of pressure supplied by the elements 5 and 6 are controlled by the valve shown in FIG. 7, so that the pressure between the walls 2 of the diaphragms drops after systole (FIG. 3) and the volume of the passage between the walls 2 is reduced so that the walls return to their initial position or diastole.

An electrical

V-F convertor can be utilized in the artificial heart of the present invention and which is generally known. The convertor converts direct current from battery or accumulator which is supplied to the input of the converter. After passing through the transformer the current is supplied to the oscillator. From the latter the impulse current is supplied in form of triangular or rectangular pulses (see FIG. 14). In the above described electrical converter 4, see FIG. 1 the shape of the pulses is formed by changing parameters of elements of the oscillator.

Figure 1B:
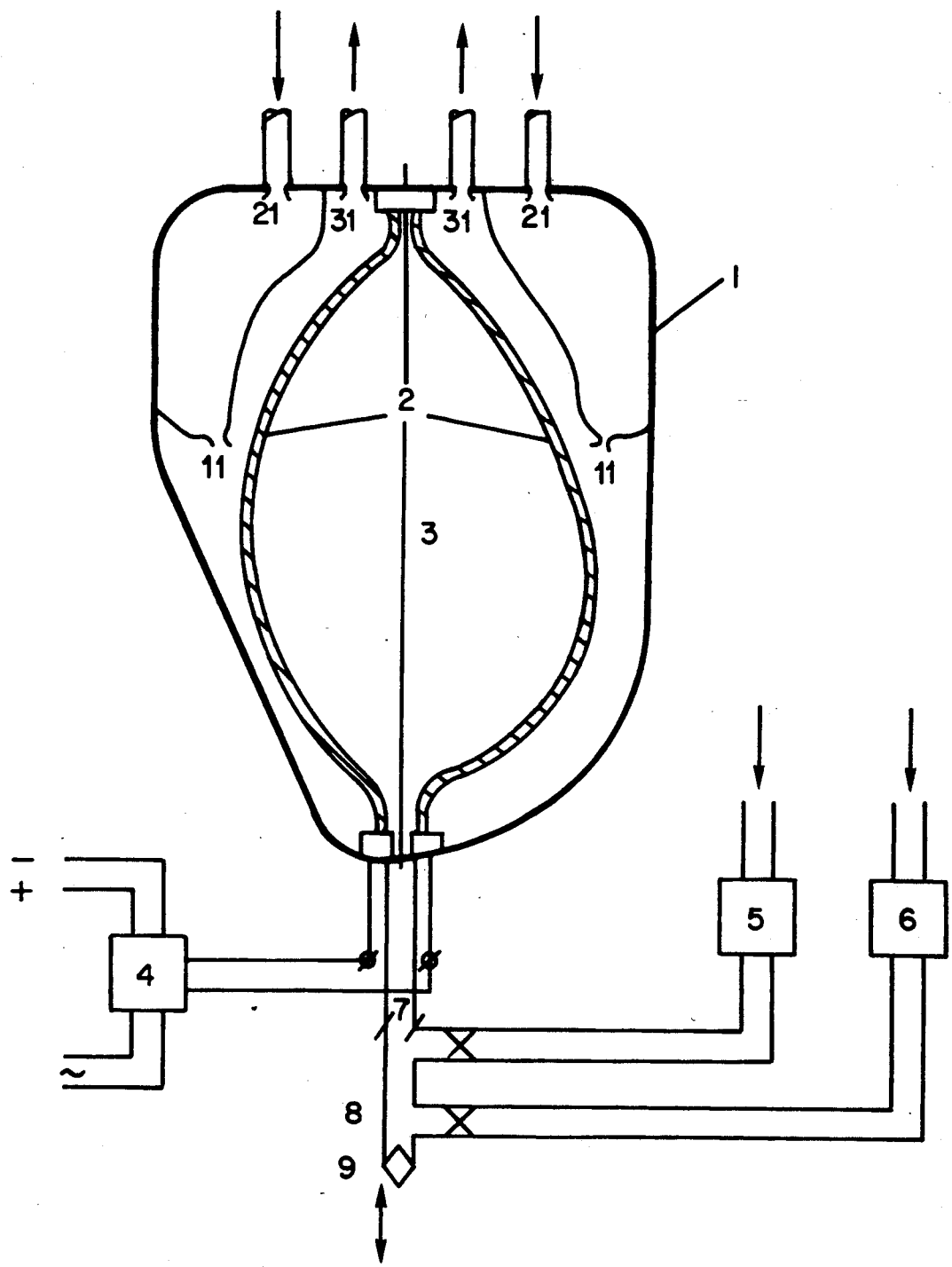
Figure 5:
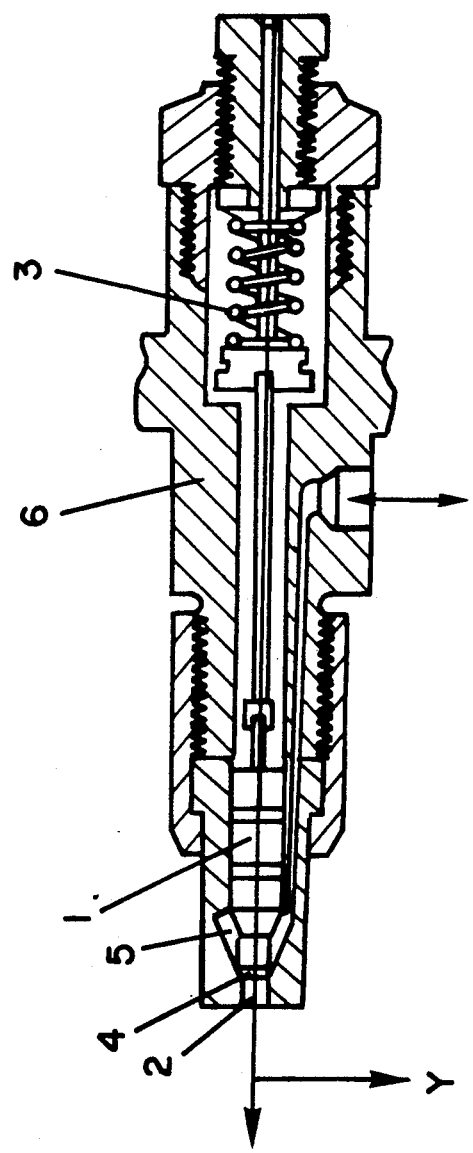
FIG. 5 shows a construction of a fluid pulse generator for the inventive artificial heart.

The pulse generator shown in FIG. 5 can be used for the convertors 5 and 6 of FIG. 1. It transforms a constant pressure of fluid (air, water) into an impulse pressure without outside energy sources. As described hereinabove, the artificial heart operates with the flow of fluid in both directions, toward and from the diaphragm. As for means for providing the flow of a fluid in an opposite direction for draining the volume between the diaphragms, this can be performed by well known means, for example with the use of the flow control valve shown in FIG. 6 or described in the book of D. McCloy et al "The Control of Fluid Power", J. Wiley and Sons, N.Y. Such flow control valves are manufactured by many U.S. companies, for example Miller Fluid Power, Bensonville, Ill; Chicago Pneumatics, Chicago, Ill, etc.

The flow control valve of FIG. 6 operates in the following manner. In the position shown in FIG. 6a the fluid (air) under pressure is supplied through the supply line 2' into a chamber A. Under the action of pressure applied to the plunger C and exceeding the force of the spring B, the plunger moves in the direction of the arrow. At this moment the openings 3', 5' and 7' are closed by the body of the plunger C. The plunger moves to the position which is shown in FIG. 6b, to the moment when the pressure in the chamber A is equalized by the force of the spring B. In this position the opening 1' is closed by the body of the plunger C. The opening 3' is connected by a passage 2' with the chamber A from which the discharge of the fluid via the throttle 3' starts. Simultaneously the passage 6 connects the openings 5' and 7' through which the discharge of the working fluid (air) starts from the draining line which leads to the space between the diaphragms 2 in FIG. 1. The pressure in the chamber A decreases during the time which depends on the opening in the throttle 4'. Under the action of the spring B the plunger assumes the position shown in FIG. 6a.

The operation of the pulse generator FIG. 5, is synchronized with the operation of the flow control valve of FIG. 6 automatically, via the draining line from the pulse generator to the flow control valve. In the position of FIG. 7a the draining line is closed by the plunger C, and the discharge of the working fluid (air) takes place into the space 3 of the heart between the diaphragms 2. In the position shown in FIG. 6b, the draining line is opened through the flow control valve (the passage 6' connects the openings 5' and 7'), the pressure under the plunger of the injector drops, and the supply of fluid to the heart stops.

This control valve can be used not only for draining of the space 3 between the diaphragms 2, but also simultaneously for transformation of the constant pressure of fluid into an impulse pressure, by means of additional passages in the plunger and housing of the valve.

Coming back again to electromagnetic convertors which can be used in the artificial heart of the present invention, it is emphasized that they are widely known in the art. It can be a convertor of DC into AC of given frequency and impulse shape. Such convertors are disclosed for example in "Switching Power Convertors", P. Wood, Van Nostrand Co., 1981, chapter 4, p. 67; "Electronic Engineer's Handbook". D. G. Fink, McGrow-Hill Book Co., 1982, chapter 14, 14–24, 14–26, 14–57 and chapter 7, 7–14. The electromagnetic convertor which can be used here can also be formed as a convertor of AC from electrical network (120, 50 Hz) into direct sign-alternating current with frequency of approximately 60 Hz and voltage of at most 8 v. Such convertors are also well known, for example from the above "Switching Power Convertors" chapter 5 and 7; "Electronic Engineer's Handbook" chapter 16-6; "Thyristor Phase Controlled Convertors and Cycloconvertors", B. P. Pelly, J. Willy & Sons, N.Y., 1971; "Static Power Frequency Changers". L. Gyugyi & B. P. Pelly, J. Willy & Sons, N.Y., 1975. Direct- to -alternating current convertors are manufactured for example by Magnetic Inc., Hybrid Systems Corp., Voltex Co., Micro Curcuit Engineering Inc. Voltage-to-frequency convertors are manufactured by Dymec Inc., Analog Devices., Solid State Electronics Inc.

The strength of the magnetic field to move the blood in the artificial heart can be determined as follows. For pumping of 50 ml per sec. and pressure of 130 mm Hg, the power of the diaphragm must be:

$$p = 0.2 kg/cm^2 \times 0.05 ml/sec = 0.02 kwt\ (20w).$$

This power can be obtained from a source of AC through AC-AC convertor, or from a battery of DC through DC-AC convetor.

When the magnetic field is used for displacement of the walls 2 of the diaphragm from the heart chambers, a magnetic flux which is required for this purpose is $$B = \sqrt{\frac{2f \times \mu_o}{A_a}},$$

wherein f is a force of attraction or spreading of the walls 2, $v_o$ is a magnetic permeability of the medium (for air it is equal to $4 \times 10^{-7}$ weber/amp. m. or T·m/A) $A_a$ is an area of a cross section of the passage between the walls in m.

$$B = \sqrt{\frac{2 \times 1000 \times 4\pi 10^{-7}}{0.1}} = 0.05\ weber/meter$$

see "Introductory Electrical Engineering", C. F. Corcoran, J. Willy & Sons, N.Y.

The emergency system through the elements 5 and 6 from a source of water or compressed air operates in the following manner.

A required water main with a water pressure of up to 30 psig is connected to the hydraulic convertor 5 or a short pipe which leads to the latter, by means of a well known rubber hose or plastic pipe. Convertors of a constant water pressure into an impulse water pressure are known, such as for example sprinklers for irrigation, hydraulic flow control valves as described above, hydraulic relief valves, fluid injectors of Diesel engines, etc. They are described for example in "The Control of Fluid Power", D. McCloy & H. R. Martin, J. Willey & Sons, FIGS. 12.11, 12.7; "Marck's Standard Handbook for Mechanical Engineers" McGrow-Hill Book Co., FIG. 45. The latter discloses the convertor or pulse generator shown in FIG. 5, in which fluid with a constant pressure is supplied under a piston 1 and lifts the latter to feed the fluid in the artificial heart through a nozzle 2, and then the pressure under the piston 1 drops and the piston 1 is spring-biased 3 ontoi the seat 4 so that the fluid feed is stopped. After closing of the nozzle 2 the pressure under the piston 1 increases again and the fluid goes into the artificial heart. The frequency of pulses depends on tensioning of the spring, volume of the cavity 5 under the piston 1, nozzle 2 outlet size, which can be adjusted to adjust the frequency of pulses and quantity of liquid supplied with each pulse. The hydraulic converter can be used in the inventive artificial heart.

Compressed air line is available in all industrial enterprises, even at gas stations, and usually has the pressure up to 90 psig. Constant pressure is converted into a pulse pressure by known convertors which are similar to the hydraulic convertors described hereinabove. An example of such convertors is a pneumatic hammer drill used in construction and earth works. They are also described in the above "Marks' Standard Handbook for Mechanical Engineers". In the artificial heart in accordance with the present invention the discharge of the system between the pulses is performed by the flow control valve together with the pulse converter. The air pulse pressure can also be supplied by a hand pump, for example a diaphragm pump which is used in systems of artifical blood circulation for a long time. They are described, for example in "Hydraulic Pumps Handbook", V. Karasic McGrow-Hill-Book Co., N.Y. 1981; "Fluid Flow", N. P. Cherimsinov, Ann Arbor Science Publishers, Ann Arbor, Mich, FIG. 120. Proper pulsating flow can be established very easy by diaphragm displacement control valve or by using a relief valve on the discharge side of the pump. Other approaches to pulsating systems are also disclosed in E.M. Mogendovich "Hydraulic Pulse Systems", Mashinostroenie, Leningrad, 1977; E. M. Mogendovich "Simulation of Wave Phenomenon in Blood Circulating Systems in Advanced Bioengineering", ASME WAM, Boston, 1983; E. M. Mogendovich "Hydropulse Systems and Technology in the USSR", Delphic, Va. 1985.

The element 9 operates by breathing or in other words by introducing air into the passage 3 by supplying air from a mouth of a person.

The important feature of the present invention is that the inventive artificial heart operates closer to the natural heart and reduces or eliminates the danger of strokes or vessel damages connected with the pulse shape. It was found that in the natural heart the shape of the blood pressure pulse is such that there is a wave effect in the heart vessels, and as a result there are openings of blood vessels by the wave pressure which goes ahead of the blood flow and can stretch the flexible walls of the blood vessels. This pulse phenomenon of a natural blood circulating system can be easily detected by a finger, which when being put on a wrist, feels a wave pressure speeding along a blood vessel, and as a result the stretching of the walls of the vessel.

Because of physiological requirements, a body has to be supplied with a particular quantity of blood in a normal condition. The quantity of blood per pulse (volumetric velocity) is a function of a pressure drop (difference between systolic and diastolic pressure) in the blood circulating system. The phenomenon of the peripheral blood pressure pulsation is well known as a "phenomenon of a peripheral heart". The physics of it is described in applicant's research "Simulation of Wave Phenomenon in the Blood Circulating System", Advance in Bioengineering, ASME, 1984, and monograph "Hydropulse Systems and Technology in the USSR", Delphic, Falls Church Va, 1985, p.44. The wave phenomenon increases cross-sectional area of blood vessels and helps the heart to circulate the same volume with a reduced blood pressure.

Simulation of the wave phenomenon which is performed in the artificial heart in accordance with the present invention by simulating a natural blood pulse shape with a steep front of the pulse reduces the blood pressure in the blood circulating system and thereby reduces or eliminates the danger of damages to the vessels. In the artificial heart with the simulation of the wave shape the blood pressure can be reduced by 47% for circulating the same amount of blood.

It is well known that the high pressure in a blood circulating system may cause a damage of blood vessels.

The wave phenomenon in an aritficial heart reduces the blood pressure in the blood circulating system. The wave phenomenon can be simulated only by simulating a natural blood shape pulse, which first of all includes a very steep front of the pulse. The steep front which is described as $$\frac{d^2p}{dt^2}$$

induces the wave phenomenon in the blood circulating system (compare with a water hammer in a water supply system). The indirect proof of the influence of the pulse shape consists in the fact that all operations made with existing artificial hearts (mostly Jarvik-7) which did not simulate the natural pulse shape were accompanied by damages to peripheral blood vessels in patients.

It has been determined that in an artificial heart with simulation of the wave shape the blood pressure can be reduce by 47% for circulating the same amount of blood. The systolic blood pressure drop is $$\Delta p = \frac{Q^2 \times v}{\mu^2 \times A^2 \times g},$$

wherein
$\mu$—hydraulic coefficient of resistance (0.7),
Q—volumetric velocity of blood flow (cm$^3$/sec).
A—area of vessel cross section (cm$^2$),
g—gravity acceleration (cm/sec$^2$),
v—specific blood density (g/cm$^3$).

For a system without the wave phenomenon (no pulse shape simulation) $\Delta p = 87.6$ g/cm$^2$=61 Hg mm.

For a system with the wave phenomenon (pulse shape simulation) $\Delta p = 44$ g/cm$^2$=33 Hg mm.

As mentioned herein above the diaphragms can contain coils to produce magnetic repulsion and attraction.

It is also possible to use purely electric charge forces between the diaphragms.

The level of a current to be used, can be determined from the formula $$i = \frac{2B(r^2 - l^2)^{3/2}}{r^2 \times 4\pi \times 10^{-7} \times \mu_r}, \text{ wherein}$$

wherein
r—radius of a coil,
l—distance between coatings of the diaphragms,
$\mu_r$—relative permeability.

With only one coil the level of current can be between 5 and 20 amp. However, it is possible to use thousands coaxial and coplanar coils in the coatings, in which case the level of the current can be between 0.1 and 1 amp.

A purely electric charge forces between the diaphragms, can be determined from the formula $$F = \frac{Q1 \times Q2}{4\pi \times \epsilon_o R^2}, \text{ wherein}$$

wherein
$\epsilon$—is air permittivity equal to $8.85 \times 10^{-12}$ F/M,
Q1, Q2—charges on the ferromagnetic coatings,
R—distance between the diaphragms (see "Standard Handbook for Electrical Engineers' Finn & Carol, McGraw-Hill, p.2-29). With Q1=Q2, Q=$10.54 \times 10^{-6}$ C.

The invention is not limited to the details shown since various modifications and structural changes are possible without departing in any way from the spirit of the present invention.

What is desired to be protected by Letters Patent is set forth in the appended claims.

I claim:

1. An artificial heart, comprising
a housing;
means in said housing forming two auricle chambers and two ventricle chambers separated from one another;
mens for communicating each of said auricle chambers with a respective one of said ventricle chambers;
blood inlet means in each of said auricle chambers;
blood outlet means in each of said ventricle chambers;
two flexible diaphragms arranged in said housing and provided with elements which form an electromagnetic field under the action of electric current and which are connectable with an electric source so that said diaphragms expand and contract in response to supply of electric current from said electric source and therefore displace blood from said auricle chambers into said ventricle chambers, and from said ventricle chambers outwardly of said housing; and
means for expanding and contracting said flexible diaphragms by a fluid and including a passage between said diaphragms and a connecting element adapted to connect said passage with a source of the fluid.

2. An artificial heart as defined in claim 1, wherein said elements which form an electromagnetic field are coatings provided on said diaphragms.

3. An artificial heart as defined in claim 1; and further comprising an electromagnetic converter means for converting a direct current into an alternating current, said electromagnetic converter means being connected with said elements which form an electromagnetic field.

4. An artificial heart as defined in claim 1, wherein said connecting element comprises means for connecting said passage with a source of water used as said fluid and further comprising a hydraulic converter means for converting a constant pressure of water from said source of water into a pulse water pressure and to supply water under the pulse water pressure to said passage.

5. An artificial heart as defined in claim 1, wherein said connecting element comprises means for connecting said passage with a source of compressed air used as said fluid; and further comprising a pneumatic converter means for converting a constant pressure of air from said source of compressed air into a pulse air pressure and to supply air under the pulse air pressure to said passage.

6. An artificial heart as defined in claim 1, wherein said connecting element comprises means for connecting said passage with a respiratory system of a person actuating the artificial heart.

7. An artificial heart as defined in claim 1; and further comprising an electromagnetic converter means for connecting said electric source with said elements which form an electromagnetic field and means supplying said elements with a current that expands and contracts said diaphragms in a manner displacing the blood with a pressure pulse substantially similar to a pressure pulse of a natural heart.

8. A method of operating an artificial heart having two auricle chambers and two ventricle chambers arranged so that each auricle chamber is connected with the respective ventricle chamber and each auricle chamber has a blood inlet while each ventricle chamber has a blood outlet, the method comprising the steps of:
providing two diaphrams with elements which form an electromagnetic field;
supplying electric current to said elements to expand and contract said diaphragms in response to said electric current supply and thereby displace blood from said auricle chambers into said ventricle chambers, and then from said ventricle chambers outwardly;
providing two diaphragms as defined in claim 1 with a passage between said diaphragms; and
supplying into the passage between said diaphragms at least one fluid, when the diaphragms are disconnected from a source of electric power, to expand and contract said diaphragms under the section of said fluid and thereby displace the blood.

9. A method as defined in claim 8, wherein said step of supplying electric current includes supplying such electric current that said diaphragms expand and contract to produce a blood displacement with a blood pressure having a pulse shape substantially corresponding to a pulse shape produce by a natural heart.

10. A method as defined in claim 9, wherein said pulse shape of said blood pressure of said blood displacement has a steep forward flank.

* * * * *

UNITED STATES PATENT AND TRADEMARK OFFICE
CERTIFICATE OF CORRECTION

PATENT NO. : 5,139,516

DATED : August 18, 1992

INVENTOR(S) : Eugene Mogendovich

It is certified that error appears in the above-identified patent and that said Letters Patent is hereby corrected as shown below:

Title page, item [76], change

"Eugene Mogendovich" to-"Eugene M. Mogendovich"- change "41 Bunker" to-"41 Bunker Road"- change "Hannover" to-"Hanover"-

Figure 1C:
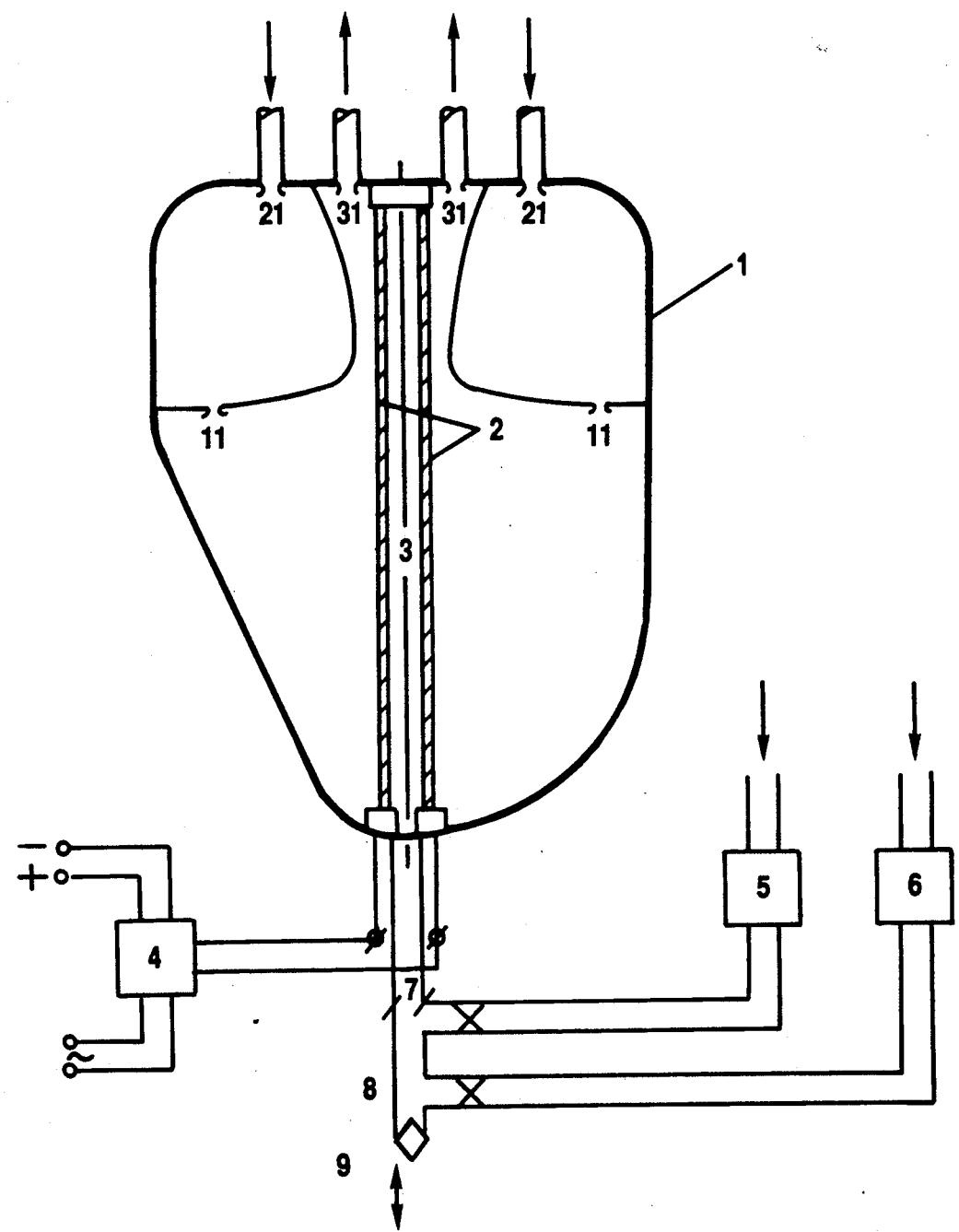
Figure 4B:
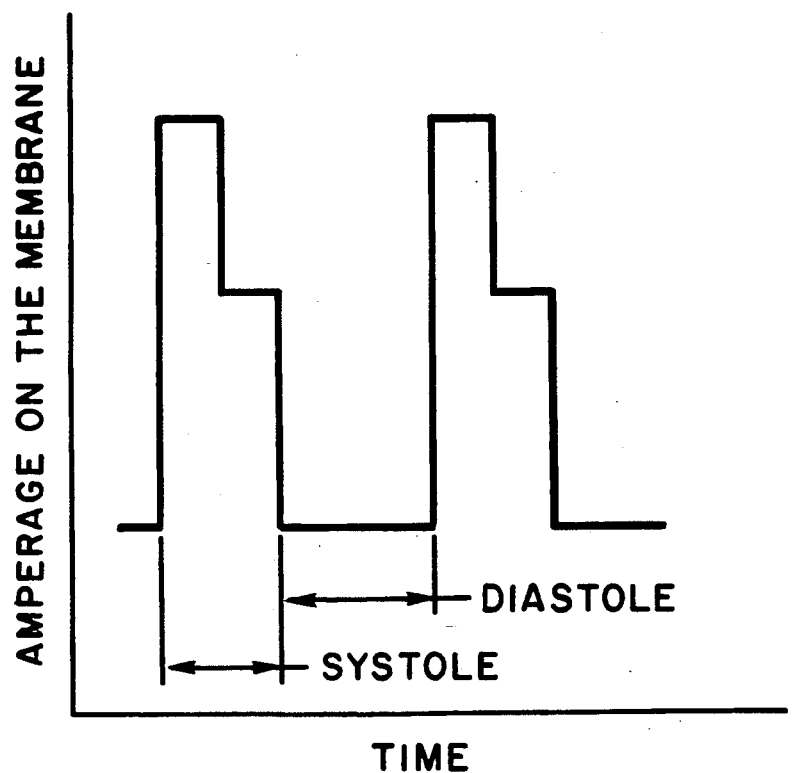
Figure 6A:
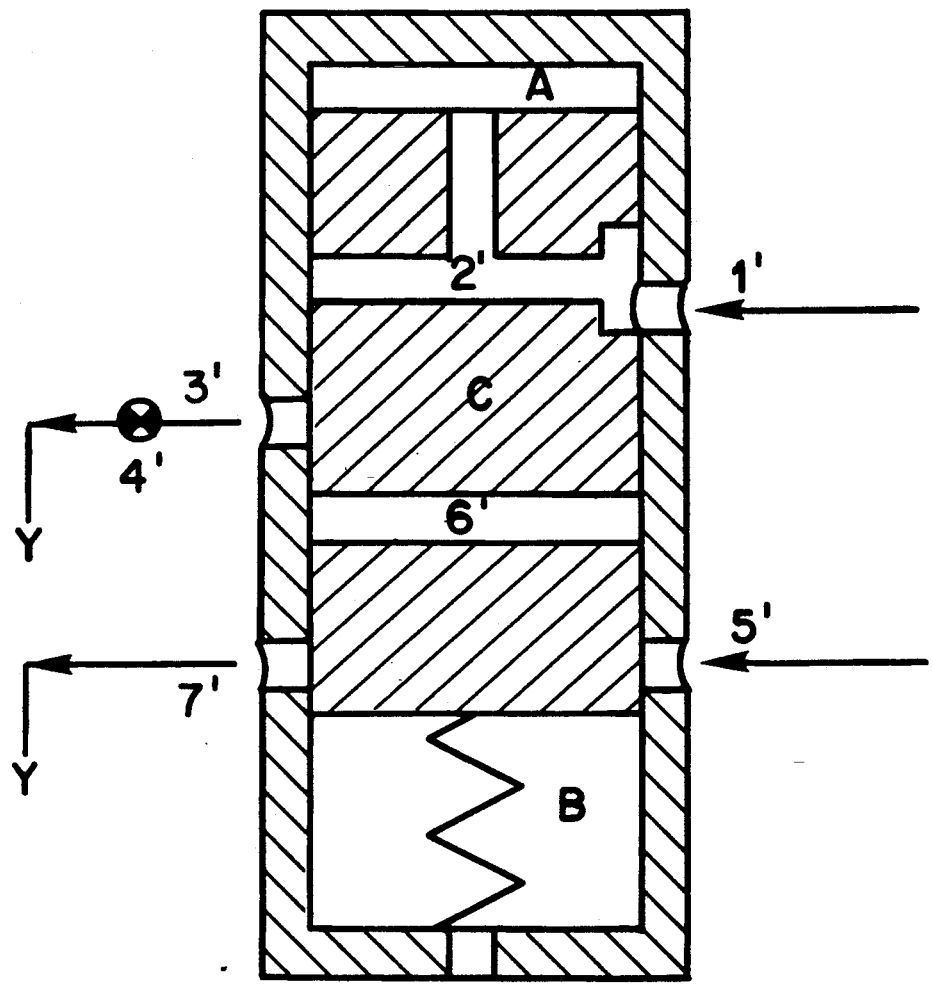
FIGS. 6A, 6B shows a flow control valve for the inventive artificial heart.
Figure 6B:
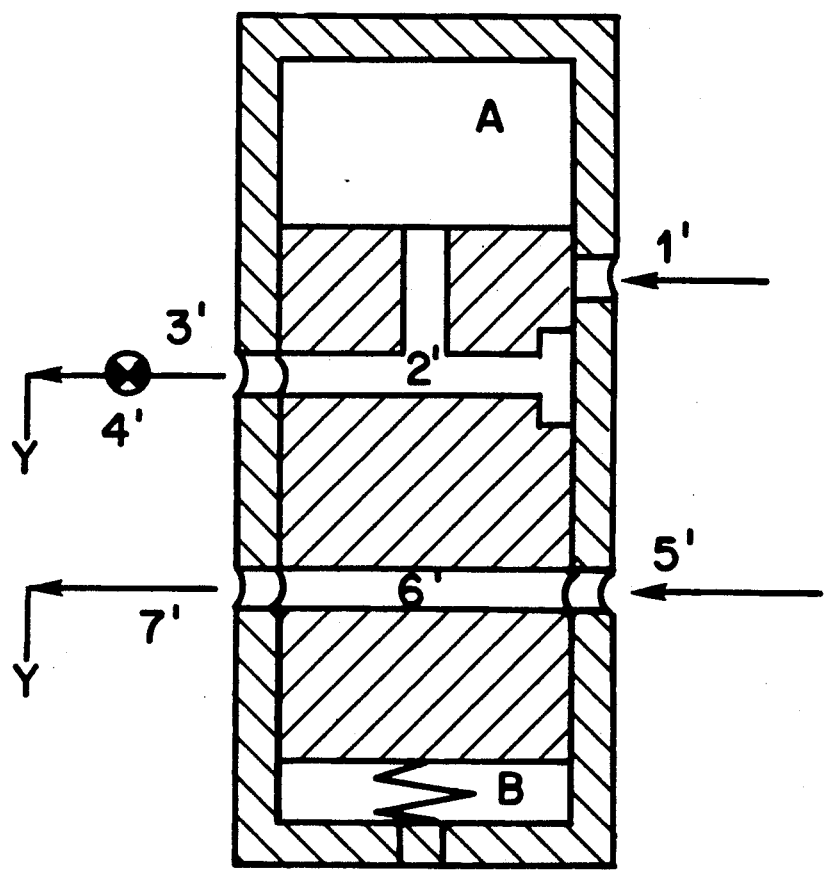

Column 5, line 2, "Fig.7" should be -"Fig.6"-
Column 5, line 3, "Fig.3" should be -"Fig.1c"-
Column 5, line 14, "Fig.14" should be -"Fig.4b"-
Column 5, line 61, "Fig.7a" should be -"Fig.6a"-
Column 9, line 10, "wherein" should be omitted
Column 9, line 26, "wherein" should be omitted Signed and Sealed this Twenty-fourth Day of August, 1993

Attest:

BRUCE LEHMAN

*Attesting Officer*     *Commissioner of Patents and Trademarks*